US007760355B2

(12) United States Patent
Larsen et al.

(10) Patent No.: US 7,760,355 B2
(45) Date of Patent: Jul. 20, 2010

(54) FOCUSED DROPLET NEBULIZER FOR EVAPORATIVE LIGHT SCATTERING DETECTOR

(75) Inventors: David W. Larsen, St. Charles, MO (US); Zhi Xu, St. Louis, MO (US)

(73) Assignee: The Curators of the University of Missouri, Columbia, MO (US)

( * ) Notice: Subject to any disclaimer, the term of this patent is extended or adjusted under 35 U.S.C. 154(b) by 648 days.

(21) Appl. No.: 11/191,272

(22) Filed: Jul. 27, 2005

(65) Prior Publication Data

US 2007/0023037 A1 Feb. 1, 2007

(51) Int. Cl.
*G01N 15/02* (2006.01)

(52) U.S. Cl. ...................................... 356/335; 356/438

(58) Field of Classification Search ......... 356/335–442, 356/39–42, 72–73, 244–246; 250/339.11–339.13, 250/574, 222.2, 423 R; 436/151, 177; 422/70, 422/82.01, 83
See application file for complete search history.

(56) References Cited

U.S. PATENT DOCUMENTS 4,426,213 A 1/1984 Stavropoulos
4,958,529 A * 9/1990 Vestal .................... 73/864.81
5,529,244 A 6/1996 Horvath, Jr. et al.
5,837,826 A 11/1998 Flickinger et al.
6,024,129 A 2/2000 Schima
6,362,880 B1 3/2002 Anderson, Jr. et al.
6,750,449 B2 6/2004 Marcus
7,006,218 B2 * 2/2006 Anderson et al. ........... 356/337
2001/0001575 A1 5/2001 Anderson, Jr. et al.
2005/0045239 A1 3/2005 Krieger et al.
2007/0023037 A1 2/2007 Larsen et al.

FOREIGN PATENT DOCUMENTS

WO WO 9932174 A1 * 7/1999 ................ 356/335

OTHER PUBLICATIONS

Gilson's 350 Micro Pump, Gilson website http://www/gilson.com/Products/product.asp?pID=28.
S.L. Koeniger, S.J. Valentine, S. Myung, M. Plasencia, Y.J. Lee, D.E. Clemmer, "Development of Field Modulation in a Split-Field Drift Tube for High-Throughput Multidimensional Separations", Journal of Proteome Research 2005, vol. 4, pp. 25-35.
O.T. Nedelcu, V. Moagar-Poladian, "Modeling of the Piezoelectric Micropump for Improving the Working Parameters", National Institute for Research and Development in Microtechnologies (IMT-Bucharest).
Sedex LT-ELSD brochure, Sedere Inc., Cranbury, NJ, 2004.
Written Opinion of the International Searching Authority, Application No. PCT/US07/86640, dated Aug. 22, 2008.
International Search Report and Written Opinion issued in PCT/US2009/047029, dated Aug. 3, 2009, 11 pages.

* cited by examiner

*Primary Examiner*—Gregory J Toatley, Jr.
*Assistant Examiner*—Tri T Ton
(74) *Attorney, Agent, or Firm*—Senniger Powers LLP

(57) ABSTRACT

A focused droplet nebulizer of the invention produces substantially uniform droplets of a predetermined size. Droplets are pushed out through a small outlet orifice by the contraction of a chamber. The droplets can be carried on a substantially non-divergent path in a drift tube. A piezo membrane micro pump acts in response to an electrical control signal to force a droplet out of the outlet orifice. The nebulizer can operate at frequencies permitting a stream of individual droplets of the predetermined size to be sent along the substantially non-divergent path in the drift tube in a preferred embodiment ELSD device.

10 Claims, 7 Drawing Sheets

FOCUSED DROPLET NEBULIZER FOR EVAPORATIVE LIGHT SCATTERING DETECTOR

FIELD OF THE INVENTION

The invention is in the field of evaporative light scattering detection.

BACKGROUND

Evaporative light scattering detectors (ELSDs) are used routinely for Liquid Chromatography (LC) analysis. In an ELSD, a liquid sample is converted to droplets by a nebulizer. As the droplets traverse a drift tube, the solvent portion of the droplets evaporates, leaving less volatile analyte. The sample passes to a detection cell, where light scattering of the sample is measured. ELSDs can be used for analyzing a wide variety of samples.

The present inventors identify the nebulizer as a limit on the effectiveness of the detection capabilities of ELSDs. One problem with conventional nebulizers is that complete solvent evaporation does not occur in the drift tube. The expanding trajectory and variable sizes of the droplets produced by conventional nebulizers contributes to the incomplete evaporation and erratic measurement performance. Droplets enter the detection cell and cause scattering that is detected. The scatter effect of droplets is indicated in conventional ELSDs by the fact that substantial scattering is detected in the absence of analytes. This droplet scattering creates a large level of background noise. Accordingly, with typical ELSDs, it is only possible to measure differential scattering, where scattering from the analyte is much greater than that from incompletely volatilized solvent droplets.

Droplets that are too small to carry sufficient analyte are also produced within the distribution of droplets produced by a conventional nebulizer. The small droplets result in analyte particles that are too small to contribute to the detection signal. However, the small droplets increase solvent vapor pressure in the drift tube. Higher vapor pressure retards evaporation in the drift tube. Incomplete evaporation leads to the background noise from scattering caused by droplets as discussed above.

If the droplet size distributions and evaporation rate were constant in the conventional ELSD nebulizers, then the resultant background noise could, to a certain degree, be accounted for in the measurement. However, the rate of incomplete droplet vaporization and their distribution (size and number) tends to change randomly with time. This causes uncertainty in the analyte signal, in addition to the substantial level of background noise.

One conventional strategy for addressing the droplet distribution problem of conventional nebulizers is to remove larger droplets. An impactor has been used in the drift tube of conventional ELSDs to intercept large droplets, which are collected and exit the drift tube through an outlet drain. Additional condensation collects on the walls of the drift tube due to the divergence of spray from the nebulizer, and also drains from the outlet drain. A percentage of the divergent spray that exits via the outlet drain includes properly sized droplets with analyte. Excluding larger droplets produced by a conventional nebulizer proves difficult in practice because the nature of the droplet distribution depends strongly on three factors: mobile phase composition, mobile phase flow rate and carrier gas flow rate. The dependence is highly interactive, which makes the spray hard to control and difficult to model. These undesirable nebulizer characteristics place extraordinary demands on the structural design of ELSD units, making their design very complicated and highly empirical.

SUMMARY OF THE INVENTION

A focused droplet nebulizer of the invention produces substantially uniform droplets of a predetermined size. Droplets are pushed out through a small outlet orifice by the contraction of a chamber. The droplets can be carried on a substantially non-divergent path in a drift tube. A piezo membrane micro pump acts in response to an electrical control signal to force a droplet out of the outlet orifice. The nebulizer can operate at frequencies permitting a stream of individual droplets of the predetermined size to be sent along the substantially non-divergent path in the drift tube of a preferred embodiment ELSD device.

DETAILED DESCRIPTION OF THE PREFERRED EMBODIMENTS

The problems inherent with the use of a conventional nebulizer ultimately limit performance in evaporative light scattering detectors (ELSDs). Size, complexity, and cost are also adversely affected by the nebulizer. The invention provides a focused droplet nebulizer. A nebulizer of the invention produces substantially uniform sized droplets. Preferred embodiment nebulizers also provide a precisely controlled droplet production rate and deliver droplets along a focused path. An ELSD of the invention uses a focused droplet nebulizer to reduce background noise and improve the state of ELSD detection.

A preferred embodiment focused droplet nebulizer includes a piezo membrane micro pump. The piezo membrane micro pump has an inlet with a check valve that allows liquid to flow one way into the pump. When the piezo membrane expands, liquid is drawn into the pump and when the piezo membrane contracts, liquid is forced out a tiny outlet orifice. This creates a small single droplet. The check valve ensures that little liquid flows back through the inlet port. The droplet output is strictly controlled by an electrical signal. In other embodiments, a plurality of orifices and/or piezo membrane elements are used to produce parallel droplet streams.

Dimensions of the focused droplet nebulizer are set to produce droplets of a predetermined size. Dimensions may be set, for example, to produce droplets anywhere within in the approximate range of between 10 and 100 µm, which are sizes typically of interest in ELSD systems. Droplets in a particular physical embodiment constructed in accordance with the invention have a very narrow size distribution, typically 5% standard deviation. Applied to an ELSD, substantially all droplets will contribute to the detection signal. The rate of droplet production is controlled independently by electrical signal, e.g. a periodic signal, fed to the micro pump. Thus, the rate of droplet formation can be easily varied so as to optimize the signal to noise ratio. The droplet size is independent of droplet production rate and is not strongly dependent on liquid composition. There is substantially no divergence in the droplet path, typically 1-2 degrees standard deviation. Operation can be independent of the flow rate of the carrier gas. Piezo element micro pumps have a relatively low cost, tolerate a wide range of organic and aqueous liquids, and have a relatively long lifetime.

Preferred embodiments of the invention will now be discussed with reference to the drawings. The particular exemplary devices will be used for purposes of illustration of the invention, but the invention is not limited to the the particular illustrated devices.

Figure 1:
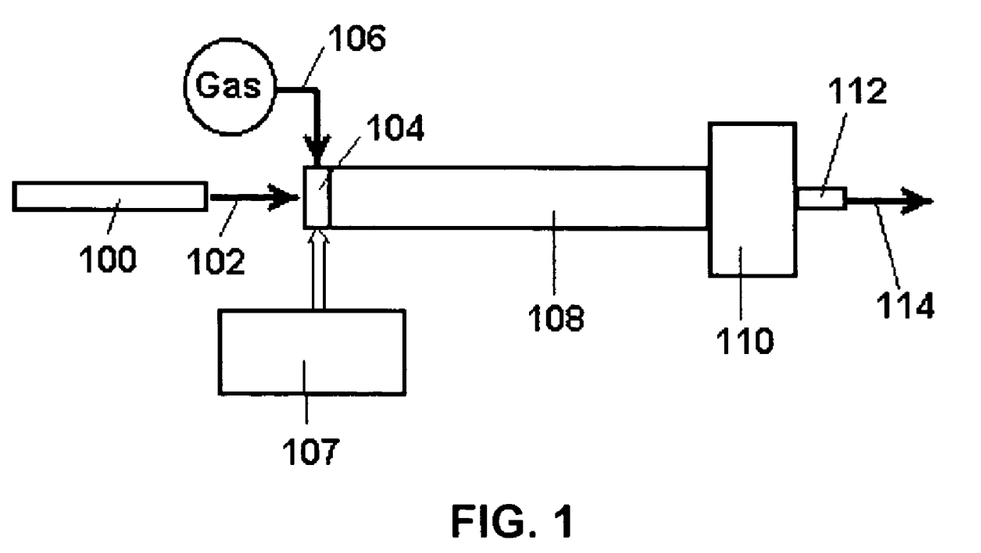
FIG. 1 illustrates an evaporative light scattering detector (ELSD) including a focused droplet nebulizer in accordance with a preferred embodiment of the invention.
Figure 2:
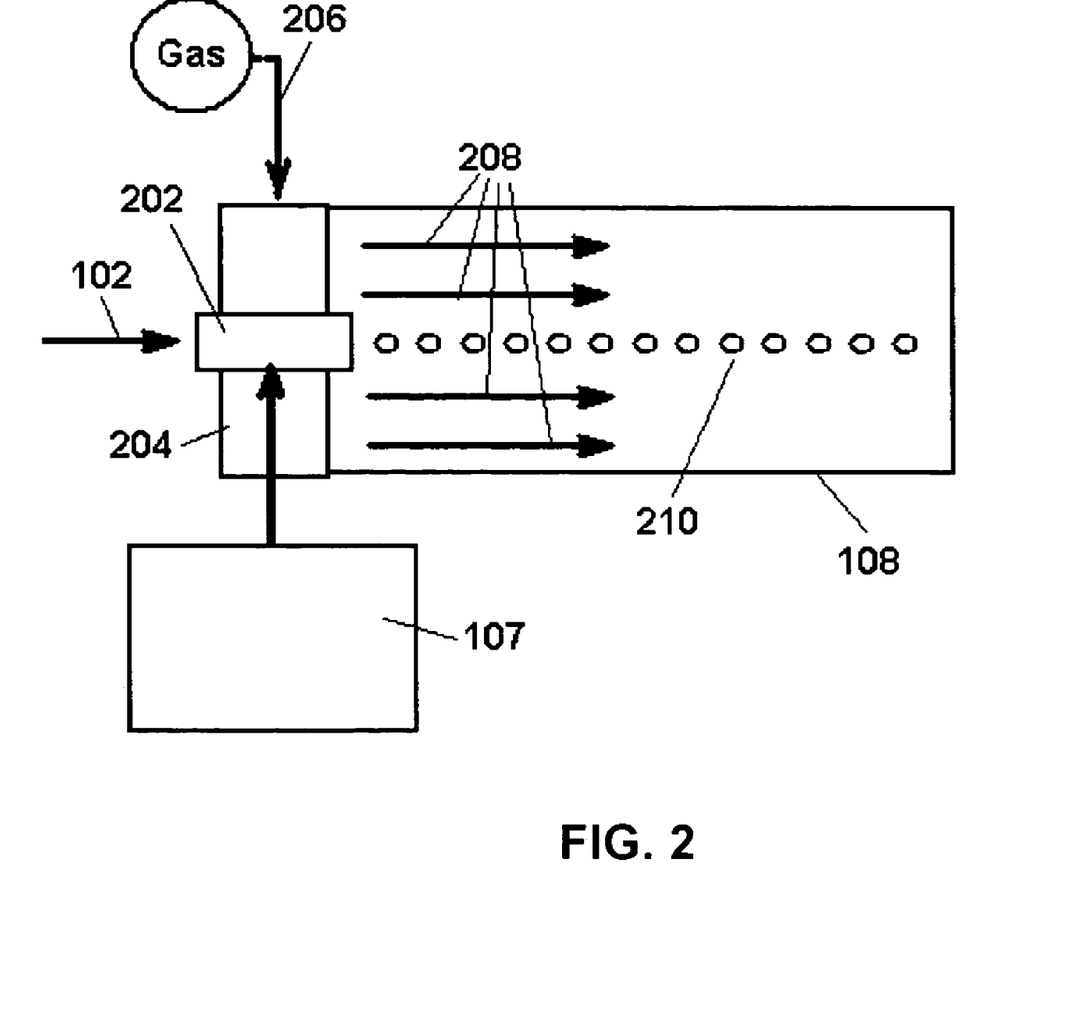
FIG. 2 illustrates the focused droplet nebulizer of FIG. 1.
Figure 3A:
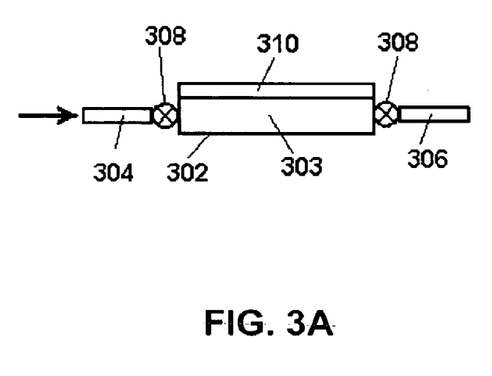
FIGS. 3A and 3B illustrate a piezo membrane micro pump of the nebulizer of FIGS. 1 and 2.
Figure 3B:
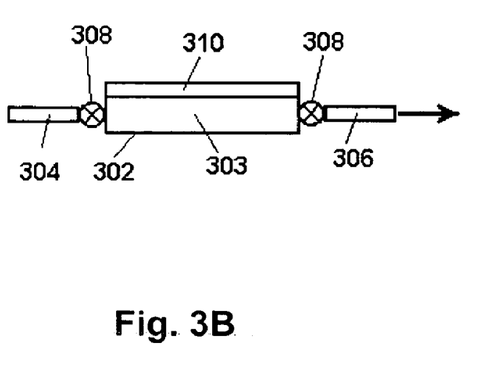
Figure 4:
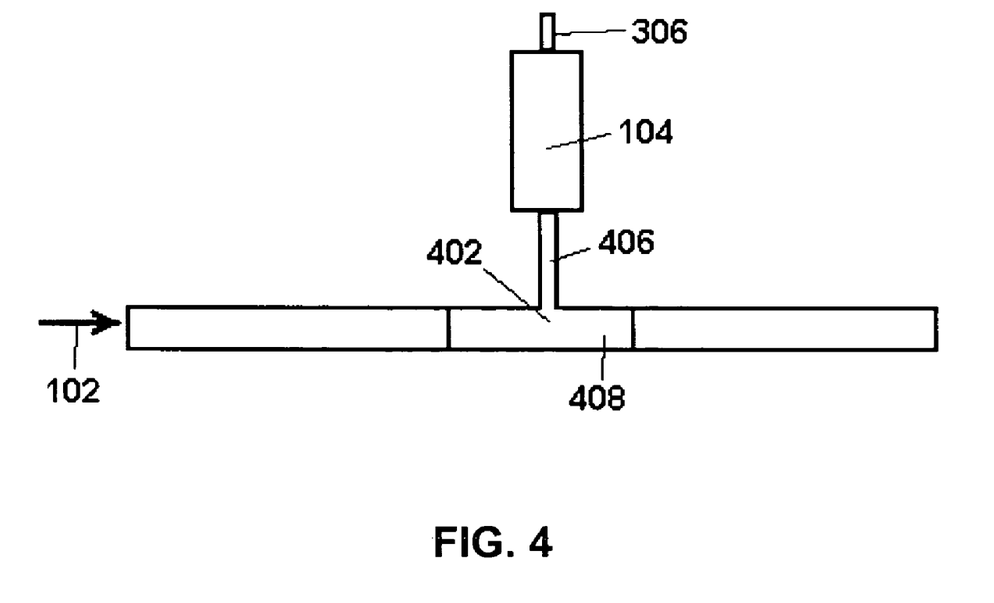
FIG. 4 illustrates a structure for reduced flow sampling of effluent in accordance with an embodiment of the invention.
Figure 5:
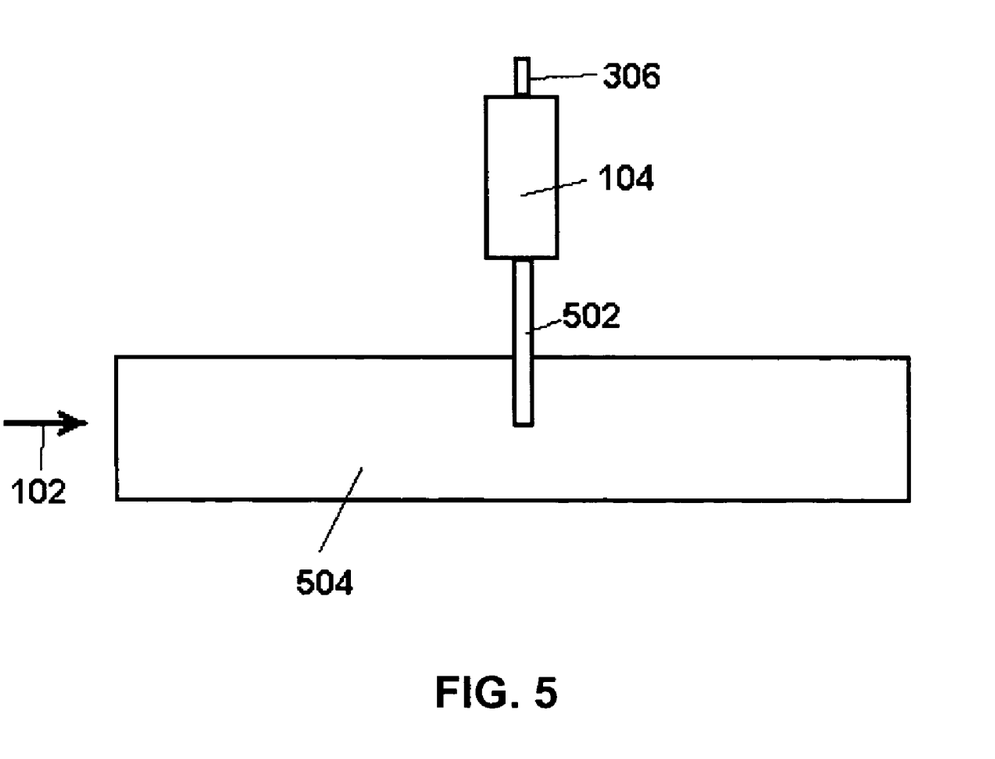
FIG. 5 illustrates a structure for reduced flow sampling of effluent in accordance with another embodiment of the invention.
Figure 6:
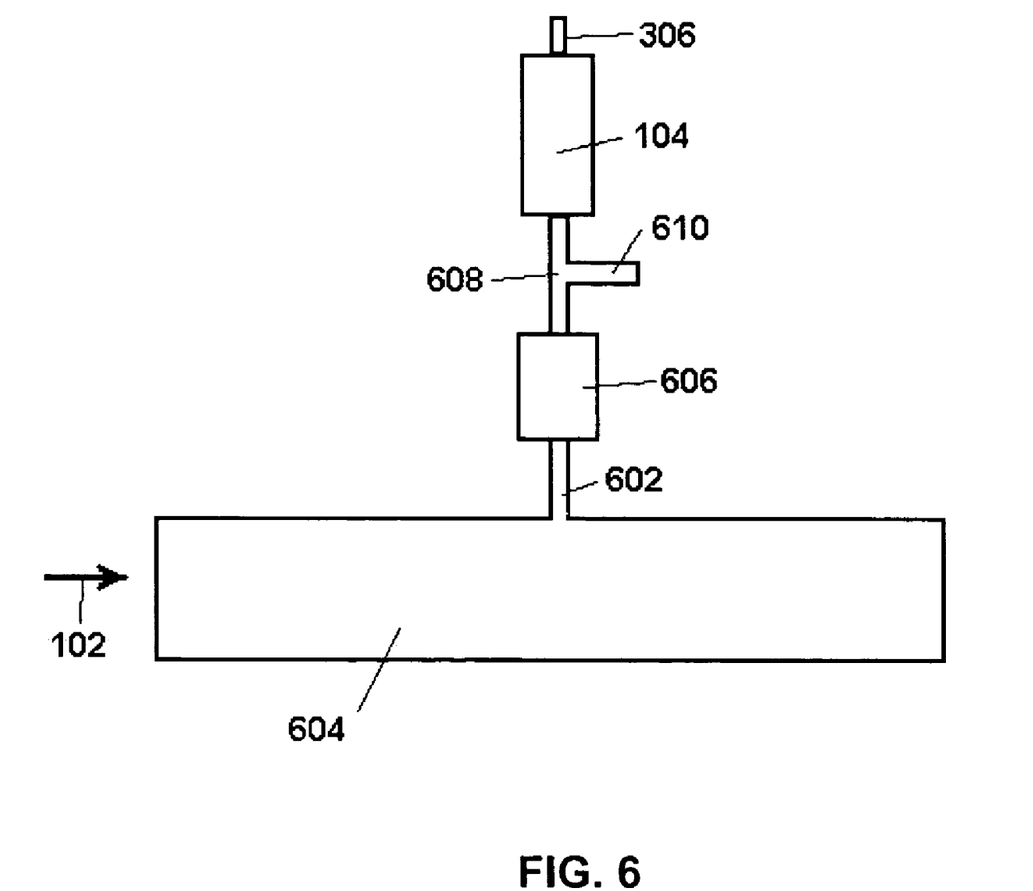
FIG. 6 illustrates a structure for reduced flow sampling of effluent in accordance with another embodiment of the invention.
Figure 7A:
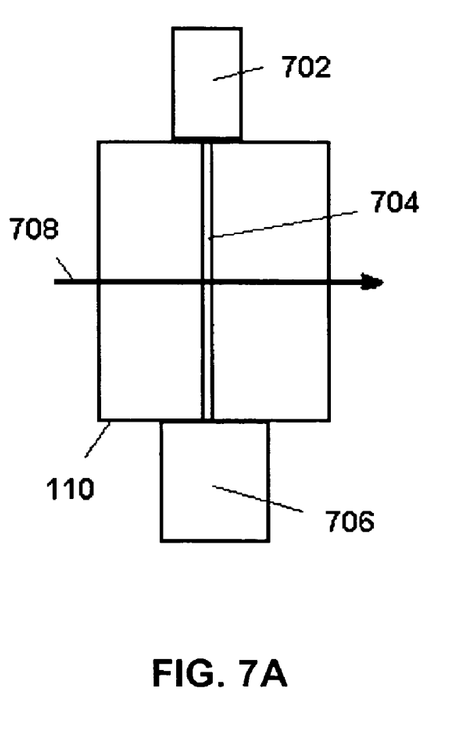
FIGS. 7A and 7B illustrate an optical detection cell of the ELSD of FIG. 1.
Figure 7B:
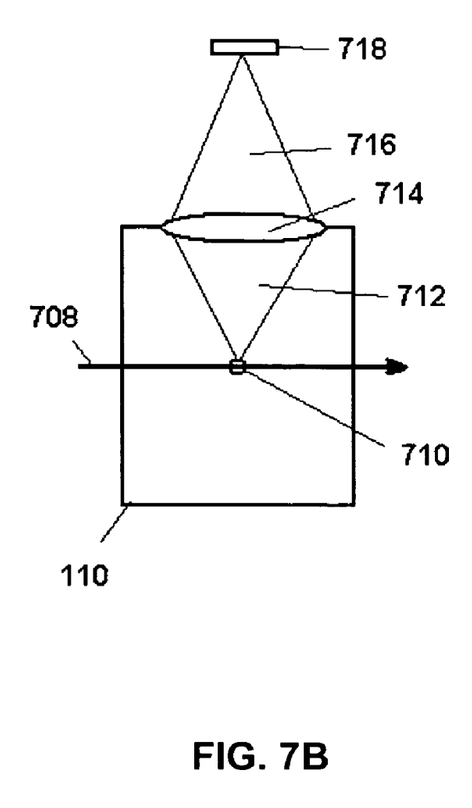

FIG. 1 illustrates a preferred embodiment ELSD including a focused droplet nebulizer. A liquid chromatography (LC) column 100 provides effluent 102 (a.k.a. the mobile phase) to the focused droplet nebulizer 104. The focused droplet nebulizer also is provided with carrier gas 106. A controller 107 controls the droplet production of the focused droplet nebulizer 104. Under control of signals from the controller 107, the nebulizer 104 produces droplets of a predetermined size that depends upon the physical characteristics of a piezo membrane micro pump in the focused droplet nebulizer. For example, droplets in the approximate range of between 10 and 100 µm, which are of interest to ELSD systems, are readily produced by a piezo membrane micro pump.

The focused droplet nebulizer 104, under control of the controller 107, produces substantially uniformly sized droplets, e.g., droplets having a very narrow size distribution, typically 5% standard deviation. The rate of droplet production is controlled readily by an electrical signal, e.g., a periodic signal, provided to the micro pump by the controller 107. The rate of droplet formation can be varied by the controller 107 to optimize the signal to noise ratio. This can be an automatic optimization provided by the controller 107, or can be an optimization conducted with operator input to the controller 107. Droplet size is independent of droplet production rate and is substantially independent of liquid composition.

The focused droplet nebulizer 104 sends the uniformed sized droplets on a substantially non-divergent focused path, typically 1-2 degrees standard deviation, into the flow of carrier gas down a drift tube 108, which is a heated section of tubing through which gas/droplets flow, and in which evaporation occurs. The mobile phase (solvent) tends to evaporate as the droplet stream passes along drift tube 108. The gas stream enters an optical cell 110, which is the detection module of the unit. The stream passes through the cell 110 and out an exit port 112 as a waste gas steam 114.

The basis of the detection method is the amount of light scattered within the detection cell 110. Ideally, scattering will arise only from substances (analytes) dissolved in the mobile phase and scattering from the mobile phase per se will be negligible. In the ideal case, all mobile phase molecules will be converted to gas in the drift tube 108, and will produce little or no scattering in the optical cell 110. Analytes, if present, will not vaporize but will be left as airborne particles, which produce substantial light scattering as they pass through the optical cell 110. Thus, if the mobile phase 102 contains an analyte, light scattering will be observed within the cell 110, whereas if the mobile phase 102 contains no analyte, little or no light scattering will be observed within the cell 110. With this situation, whenever an analyte exits the LC column, an analyte peak (strong scattering by particles) will be observed above the baseline (weak scattering by solvent).

Evaporation is highly efficient in the ELSD of FIG. 1, as the focused droplet nebulizer 104 produces substantially uniform sized droplets along a substantially non-divergent path. The problems of conventional nebulizers that include droplet size distributions and divergent sprays are avoided and background noise in the detection signal is substantially reduced. The conventional nebulizers include a spray nozzle that produces a large number of too small and too large droplets on a divergent spray. The particles that are too small do not contribute to the signal; however, they increase the solvent vapor pressure, which decreases the efficiency of the drift tube by retarding solvent evaporation. The large droplets tend to undergo incomplete vaporization and their distribution (size and number) changes randomly with time. Thus, they produce baseline noise in the absence of analyte as well as uncertainty in the analyte signal itself. The ELSD of FIG. 1 solves such problems.

FIG. 2 shows the focused droplet nebulizer 104 of FIG. 1. The focused droplet nebulizer makes use of a piezo membrane micro pump 202. Piezo membrane (aka diaphragm) micro pumps use, for example, a piezo-ceramic element as the diaphragm/membrane. Piezo membrane micro pumps are available from a number of commercial sources.

Within the focused droplet nebulizer 104, the piezo membrane micro pump 202 receives the mobile phase 102. The mobile phase 102 enters the micro pump 202, which is centrally mounted in a gas manifold 204. Carrier gas 206 enters the manifold 204 and exits into the drift tube 108 in a concentric manner around the micro pump 202. The gas manifold gives a uniform flow of gas to carry the droplets into the drift tube 108. Substantially uniform droplets 210 are produced by the micro pump 202 at a size determined by the micro pump outlet orifice and at a rate determined by the frequency of the signal applied to the micro pump piezo by the controller 107. The droplet path is substantially non-divergent and unidirectional as shown and is carried along by the carrier gas stream 208.

FIGS. 3A and 3B illustrate additional details and operation of the micro pump 202 of the nebulizer 104. The micro pump 202 has a body 302 that defines a chamber 303. Each of an inlet 304 and outlet orifice 306 includes a check valve 308. A piezo membrane/diaphragm 310 is an integral part of the chamber body 302. FIG. 3A illustrates a liquid intake action. An electrical signal (pulse) is sent to the piezo membrane 310 from the controller 107, causing it to move such that the chamber volume is increased and liquid is pulled into the chamber body through the inlet 304. The check valve 308 on the outlet orifice 306 eliminates flow into the chamber through the outlet orifice 306. FIG. 3B illustrates droplet formation and expulsion, which occurs when the piezo membrane 310 moves such that the chamber volume is decreased and liquid is forced through the outlet orifice 306 in the form of a droplet. The check valve 308 on the inlet 304 eliminates liquid flow back through the inlet 304. The rate of droplet formation is controlled by the pulsing rate, up to about 5 kHz. Each pulse results in one droplet being expelled by the pump for "drop on demand" operation. The substantially uniform predetermined droplet size is controlled by the size of the chamber 303 and the diameter of the outlet orifice 306.

Due to the substantially consistent drop size and substantially non-divergent path, the ELSD of FIG. 1 will have a noise reduction because large droplets of conventional devices are eliminated. The ELSD will also have a higher detection signal because the droplets are uniformly sized and propagate on a path wherein substantially all of the droplets make a contribution to the detection signal. Lower carrier gas rates are required. The focused droplet nebulizer 104 also has a reduced size compared to typical conventional nebulizers. Since evaporation is more efficient, the internal size of the drift tube 108 can be decreased and the drift tube can be operated at lower temperatures than used in current typical commercial devices. Lower temperature operation can minimize signal loss for analytes that tend to partially vaporize, often referred to as semi-volatiles.

In the ELSD of FIG. 1, the focused droplet nebulizer 104 receives effluent from the LC column 100 at a lower rate than is used in conventional nebulizers. A typical conventional commercial nebulizer accepts a range of mobile phase flow rates and delivers a droplet spray consistent with the experimental liquid flow rate, which may be as high as 5 mL/min. However, the focused droplet nebulizer 104 of the invention uses a piezo membrane micro pump that delivers a fixed flow rate of droplets depending on the predetermined droplet size of the nebulizer 104 and the frequency of the control signal applied by the controller.

For example, a 100 picoliter (pL) droplet with an 8 kHz signal would require a liquid input flow rate of about 0.05 mL/min, which is much smaller than typical LC liquid flow rates used in a conventional ELSD device. Assuming an unmodified typical LC column 100, only a fraction of the column effluent will be used by the focused droplet nebulizer 104. Sampling the mobile phase effluent can be conducted in a manner that represents the actual composition of the effluent at every instant, and without requiring that the entire volume of effluent pass through the micro pump. Thus, the focused droplet nebulizer 104 can be used with a typical conventional LC column 100 with appropriate sampling, or a modified, lower rate LC column can be used.

Sampling of the effluent for reduced flow into the focused droplet nebulizer 104 can be achieved by various techniques. A structure for reduced flow sampling is shown in FIG. 4. In FIG. 4, effluent 102 is passed through a tee 402, with the focused droplet nebulizer 104 attached to relatively short tube 406 of the tee 402. The focused droplet nebulizer 104 sends liquid through its micro pump's outlet orifice 306 to the ELSD drift tube 108 (not shown in FIG. 4). Another tube 408 of the tee 402, is substantially wider and accepts the main portion of the effluent 102. The tube 406 is also relatively short to keep backpressure relatively low and permit the piezo membrane micro pump in the focused droplet nebulizer 104 to draw as much liquid as is required from the tee 402. The relative diameters of the tubes 406 and 408 are set to accommodate the flow limit of the focused droplet nebulizer 104.

Another structure for reduced flow sampling is shown in FIG. 5. The FIG. 5 structure can handle larger flows than the FIG. 4 structure. The focused droplet nebulizer 104 is attached to a very small diameter sampling tube 502, which is in turn mounted so that it penetrates into the interior of a tube 504 that carries the effluent 102. The focused droplet nebulizer 104 draws as much liquid as is required and provides focused droplet output through its outlet orifice 306.

Another structure for reduced flow sampling is shown in FIG. 6. A small diameter sampling tube 602 is attached to a main flow tube 604 carrying the effluent 102. A flow controller 606 delivers a small volume of liquid to a tee 608. The focused droplet nebulizer 104 is attached to one tube of the tee 608 and excess liquid flows out a waste tube 610. The flow controller 606 ensures that the focused droplet nebulizer 104 does not experience intolerable back pressure.

Analyte enters the optical cell 110 after traversing the drift tube 108. The optical cell is shown in FIGS. 7A and 7B. As seen in top view (FIG. 7A), a light source 702 produces a light beam 704 that travels through the cell 110 and enters a light trap 706, which minimizes stray light that can interfere with detection of the scattering due to analyte. A gas stream 708 flows through the cell 110 as shown, normal to the light beam 704. In the side view (FIG. 7B) the light beam 704, not shown, is perpendicular to the plane of the paper. Thus, the gas stream 708 in the cell 110 encounters the light beam near the center of the cell 110, within a cross section 710. Analyte particles scatter light and a portion of the scattered light 712 is refocused by a lens 714, so that the refocused light 716 strikes an optical detector 718. This detected light is measured and forms the basis for quantitation in the analysis.

While specific embodiments of the present invention have been shown and described, it should be understood that other modifications, substitutions and alternatives are apparent to one of ordinary skill in the art. Such modifications, substitutions and alternatives can be made without departing from the spirit and scope of the invention, which should be determined from the appended claims.

Various features of the invention are set forth in the appended claims.

The invention claimed is:

1. A focused droplet nebulizer for connecting with a drift tube in an evaporative light scattering detector, the nebulizer comprising:

a gas manifold having an output for releasing a flow of carrier gas into the drift tube;

a piezo membrane micro pump mounted in the gas manifold, said micro pump comprising:

a piezo membrane responsive to an electrical control signal;

an effluent input to accept liquid effluent upon expansion movement of said piezo membrane; and a droplet outlet orifice to expel a single liquid effluent droplet of a predetermined size upon each opposite movement of said piezo membrane into the drift tube; and wherein the flow of carrier gas in the drift tube receives each single liquid effluent droplet expelled into the drift tube from said droplet outlet orifice and carries the received droplets in a substantially non-divergent path through the drift tube.

2. The nebulizer of claim 1, wherein said carrier gas is directed in a concentric manner about said droplet outlet orifice.

3. The nebulizer of claim 1, wherein said droplet outlet orifice is sized such that the predetermined size of said single liquid effluent droplet is in the range of 10 and 100 μm.

4. An evaporative light scattering detector, comprising:

a nebulizer according to claim 1 including one or more droplet outlet orifices, an effluent supply to said effluent input;

a drift tube accepting the carrier gas and each single liquid effluent droplet expelled from said droplet outlet orifice;

an optical detection cell; and a controller to supply the electrical control signal at a predetermined frequency, wherein the predetermined frequency controls a rate at which each single liquid effluent droplet is expelled from the droplet outlet orifice of the piezo membrane micro pump.

5. The detector of claim 4, wherein said effluent supply comprises a liquid chromatography column.

6. The detector of claim 4, further comprising flow sampling means for reducing flow of liquid effluent from said liquid chromatography column to the nebulizer.

7. A focused droplet nebulizer for connecting with a drift tube in an evaporative light scattering detector, the nebulizer comprising:
- a gas manifold having an output for releasing a flow of carrier gas into the drift tube; and
- a piezo membrane micro pump controlled by an electrical control signal, said piezo membrane micro pump comprising:
  - a liquid effluent chamber;
  - an inlet that accepts liquid effluent into the liquid effluent chamber in response to expanding of said liquid effluent chamber; and
  - at least one droplet outlet orifice, each at least one droplet outlet orifice adapted to produce a single droplet of liquid effluent from the liquid effluent chamber in response to a contracting of said liquid effluent chamber independent of the flow of carrier gas and to expel the single droplet of liquid effluent into the flow of carrier gas, wherein the expelled droplets are carried by the flow of carrier gas in a substantially non-divergent path through the drift tube.

8. The nebulizer of claim 7, further comprising:
- a drift tube for accepting droplets of liquid effluent expelled from said at least one droplet outlet orifice.

9. The nebulizer of claim 7, wherein said at least one droplet outlet orifice and said chamber are sized to produce droplets of liquid effluent of a predetermined size in the range of 10 to 100 μm.

10. An evaporative light scattering detector, comprising:
- an optical detection cell;
- a drift tube through which a stream of liquid effluent droplets are delivered to the optical detection cell;
- a focused droplet nebulizer for producing the stream of liquid effluent droplets, said nebulizer comprising:
  - a gas manifold having an output for releasing a flow of carrier gas into the drift tube;
  - a piezo membrane micro pump mounted in the gas manifold, said micro pump comprising:
    - a piezo membrane responsive to an electrical control signal;
    - an effluent input for receiving liquid effluent from an effluent supply upon expansion movement of the piezo membrane; and
    - a droplet outlet orifice for expelling the stream of liquid effluent droplets into the drift tube, said droplet orifice outlet expelling a single effluent droplet of a predetermined size upon each opposite movement of the piezo membrane, said drift tube receiving the carrier gas and each single liquid effluent droplet expelled from the droplet outlet orifice, wherein the stream of liquid effluent droplets comprises a plurality of single effluent droplets of substantially uniform size and is carried by the flow of carrier gas in a substantially non-divergent path through the drift tube; and
- a controller to supply the electrical control signal to the piezo membrane of the micro pump at a predetermined frequency, wherein the predetermined frequency controls a rate at which each single liquid effluent droplet is expelled from the droplet outlet orifice of the micro pump.

* * * * *